United States Patent [19]

Stroppolo et al.

[11] Patent Number: 5,459,157
[45] Date of Patent: Oct. 17, 1995

[54] PHARMACEUTICAL COMPOSITION FOR OPHTHALMIC USE COMPRISING A NONSTEROIDAL ANTI-INFLAMMATORY AND A DECONGESTANT DRUG

[75] Inventors: Federico Stroppolo, Pregassona, Switzerland; Daniele Bonadeo, Varese, Italy; Luigi Virgano', Lugano, Switzerland; Annibale Gazzaniga, Rescaldina, Italy

[73] Assignee: Zambon Group S.p.A., Vicenza, Italy

[21] Appl. No.: 210,743

[22] Filed: Mar. 21, 1994

Related U.S. Application Data

[63] Continuation of Ser. No. 981,843, Nov. 25, 1992, abandoned.

[30] Foreign Application Priority Data

Nov. 27, 1991 [IT] Italy ................... MI91A3170

[51] Int. Cl.⁶ ............... A61K 31/415; A61K 31/40; A61K 31/30; A61K 31/19
[52] U.S. Cl. ............... 514/401; 514/413; 514/420; 514/448; 514/567; 514/570
[58] Field of Search ................... 514/570, 448, 514/413, 401, 772.3, 567, 420

[56] References Cited

U.S. PATENT DOCUMENTS

| | | | |
|---|---|---|---|
| 4,734,222 | 3/1988 | Winterton et al. | 252/546 |
| 4,988,728 | 1/1991 | Gerson et al. | 514/448 |
| 4,996,209 | 2/1991 | Aoki | 514/263 |
| 5,077,033 | 12/1991 | Viegas et al. | 514/668 |
| 5,110,493 | 5/1992 | Cherng-Chyi et al. | 514/413 |

FOREIGN PATENT DOCUMENTS 0240464  10/1987  European Pat. Off. ........ C11D 17/00

OTHER PUBLICATIONS

American Pharmaceutical Association, *Handbook of Pharmaceutical Excipients*, 1986, pp. 225–227.
Seghizzi et al., *Chemical Abstracts*, 118(10):87642n, 1992.
Siebenbrodt et al., *Chemical Abstracts*, 117(18):178192m, 1992.
Lanier et al., *Medline*, 83150710(AN), 1983.
Von Denffer et al., *Chemical Abstracts*, 88(13)83342d, 1977.
Chemical Abstracts, vol. 115, No. 17, Oct. 20, 1991, Columbus, Ohio Abstract No. 174581; Sulewski, Michael E. et al, "Effect of topical flurbiprofen on the intraocular pressure lowering effects of apraclonidine and timolol" p. 71, col. 2.
Chemical Abstracts, vol. 115, No. 17, Oct. 20, 1991, Columbus, Ohio, Abstract No. 174582, McCannel, Colin et al, "Topical flurbiprofen pretreatment does not block apraclonidine's effect on aqueous flow in humans" p. 72; col. 1. & Arch. Ophthamol, vol. 109, #6 1991, Chicago, pp. 810–811.
Martindale, The Extra Pharmacopoeia—XXIX Ed., The Pharmaceutical Press, 1989, pp. 872–881 ("Corticosteroids").
Ilic J., et al, Klin, MBL. Augenheilk, 184, 494–498 (1984) English Abstract.
Araie M, et al., Jpn. J. Opthalmol., 27, 535–542 (1983).
Merck Index, XI Ed., Ther–15, Ther–22, 1989.

*Primary Examiner*—Raymond Henley, III
*Assistant Examiner*—William R. A. Jarvis
*Attorney, Agent, or Firm*—Stevens, Davis, Miller & Mosher

[57] ABSTRACT

A pharmaceutical aqueous solution for ophthalmic use comprising a nonsteroidal anti-inflammatory drug, having a carboxylic group, a decongestant drug and a mixture of a polysorbate and a poloxamer.

2 Claims, No Drawings

PHARMACEUTICAL COMPOSITION FOR OPHTHALMIC USE COMPRISING A NONSTEROIDAL ANTI-INFLAMMATORY AND A DECONGESTANT DRUG

This application is a continuation of application Ser. No. 07/981,843, filed Nov. 25, 1992.

DESCRIPTION

This invention relates to a pharmaceutical composition for ophthalmic use. More particularly, it relates to a pharmaceutical composition for ophthalmic use comprising a nonsteroidal anti-inflammatory and a decongestant drug.

The inflammation of the anterior segment of the eye is a pathological condition which is concurrent with or caused by different diseases of the eye such as glaucoma, macular cistoid edema, uveitis, diabetic retinopathy and conjunctivitis or by post-surgical traumas.

Steroidal anti-inflammatory drugs, such as dexamethasone, betamethasone or other glucocorticoids give excellent results but give rise to considerable drawbacks which require a strict medical control and discourage their prolonged use [Martindale, The Extra Pharmacopoeia -XXIX Ed., The Pharmaceutical Press, (1989)].

Replacement of steroidal anti-inflammatory drugs with nonsteroidal anti-inflammatory drugs (hereinafter referred to as AINS) in the ophthalmic therapy allows the attainment of the same anti-inflammatory effects without the above-mentioned drawbacks [see, for instance, Ilic J. et al., Klin Mbl. Augenheilk, 184, 494–498, (1984), Araie M. et al., Jpn. J. Ophthalmol., 27, 535–542, (1983) and the references cited therein].

The most used AINS drugs, also in ophthalmology, generally are derivatives of arylalkylcarboxylic or arylcarboxylic acids (Merck Index, XI Ed., THER-15); that is, chemically they are characterized by a carboxylic group (COOH).

Moreover, the inflammatory processes of the eye are often accompanied by congestion of the eye itself, that is by reddening, swelling, hyperaemia and itchiness.

In the therapy of the eye inflammations it is therefore desired to associate an anti-inflammatory with a drug decongestant drug.

The inventors are not aware of any aqueous composition comprising both an AINS and a decongestant drug.

Experiments carried out by the inventors have shown that an aqueous solution comprising both an AINS, having a carboxylic group, and a decongestant drug is not stable due to the quick formation of a precipitate, usually within a few hours.

This incompatibility clearly hinders the preparation of a pharmaceutical composition in the form of an aqueous collyrium which must usually be stabile for at least 2 years.

Now, it has been surprisingly found that an aqueous solution comprising both an AINS, having a carboxylic group, and a decongestant drug can be stabilized for at least 2 years by means of a mixture of a polysorbate and a poloxamer, said mixture acting as a solubilizing agent.

Therefore, it is an object of this invention to provide a pharmaceutical aqueous solution for ophthalmic use comprising a nonsteroidal anti-inflammatory drug, having a carboxylic group, a decongestant drug and a mixture of a polysorbate and a poloxamer.

The pharmaceutical aqueous solution of this invention is stable for at least two years at room temperature and is, therefore, particularly suitable for the preparation of ready to use collyria.

The term "nonsteroidal anti-inflammatory drug having a carboxylic group" is herein used to mean an anti-inflammatory drug selected from the group comprising the derivatives of arylacetic, arylbutyric, arylcarboxylic, arylpropionic, salicylic acids and the like.

Examples of nonsteroidal anti-inflammatory drugs having a carboxylic group according to this invention are the drugs selected from the group comprising diclofenac, flurbiprofen, indomethacin, suprofen, ketorolac, and the pharmaceutically acceptable isomers and salts thereof.

Typical examples of conventional decongestant drugs suitable for topical use are the drugs selected from the group comprising apraclonidine, fenoxazoline, indanazoline, naphazoline, oxymetazoline, tetrahydrozoline, tramazoline, tymazoline and xylometazoline (Merck Index, XI Ed., THER-22), and their pharmaceutically acceptable salts.

Polysorbates are esters of polyoxyethylene(20)sorbitan with fatty acids and are widely used as surfactants in the pharmaceutical field and also in ophthalmic compositions.

Preferred polysorbates according to this invention are polyoxyethylene(20)sorbitan monolaurate and mono-oleate, known as polysorbate 20 and polysorbate 80, respectively.

Poloxamers are surfactants of the poly(oxyethylene)poly-(oxypropylene) copolymer type, commonly used in the pharmaceutical field.

A preferred poloxamer according to this is poloxamer 407; a poly(oxyethylene)poly(oxypropylene) copolymer wherein the polyoxypropylene portion has an average molecular weight of about 4000 and the polyoxyethylene portion amounts to 70% by weight.

Still more preferably, the pharmaceutical composition of this invention comprises a mixture made of 1 part by weight of polysorbate 20 and 3 parts by weight of poloxamer 407.

The pharmaceutical composition of this invention is unique as far as the components are concerned.

In fact, only the mixture polysorbate-poloxamer acts effectively as a solubilizing agent in an aqueous solution comprising an AINS drug, having a carboxylic group, and a decongestant drug.

In other words, only the mixture polysorbate-poloxamer prevents the formation of a precipitate and therefore allows a collyrium to be stable for at least two years.

A polysorbate or poloxamer alone and also other surfactants commonly used in the pharmaceutical field such as polyethylene glycol, glycerol, propylene glycol, esters of polyoxyethylene with fatty acids, nonoxynol, esters of sorbitan with fatty acids, and mixtures thereof proved to be ineffective as solubilizing agents.

Likewise, mixtures of polysorbate with polyethylene glycol, glycerol, propylene glycol, esters of polyoxyethylene with fatty acids, nonoxynol and esters of sorbitan with fatty acids (see example 8) resulted to be ineffective.

Typical examples of compositions according to this invention are:

| | |
|---|---|
| Sodium diclofenac | 0.10% (w/v) |
| Tramazoline hydrochloride | 0.0632% (w/v) |
| Polysorbate 20 | 3.00% (w/v) |
| Poloxamer 407 | 9.00% (w/v) |
| Water to 100 ml | |
| Indomethacin | 0.10% (w/v) |

-continued

| | |
|---|---|
| Tramazoline hydrochloride | 0.0632% (w/v) |
| Polysorbate 20 | 3.00% (w/v) |
| Poloxamer 407 | 9.00% (w/v) |
| Water to 100 ml | |
| Flurbiprofen | 0.03% (w/v) |
| Tramazoline hydrochloride | 0.0632% (w/v) |
| Polysorbate 20 | 3.00% (w/v) |
| Poloxamer 407 | 9.00% (w/v) |
| Water to 100 ml | |
| Sodium Diclofenac | 0.10% (w/v) |
| Tetrahydrozoline hydrochloride | 0.05% (w/v) |
| Polysorbate 20 | 3.00% (w/v) |
| Poloxamer 407 | 9.00% (w/v) |
| Water to 100 ml | |
| Indomethacin | 0.10% (w/v) |
| Tetrahydrozoline hydrochloride | 0.05% (w/v) |
| Polysorbate 20 | 3.00% (w/v) |
| Poloxamer 407 | 9.00% (w/v) |
| Water to 100 ml | |
| Flurbiprofen | 0.03% (w/v) |
| Tetrahydrozoline hydrochloride | 0.05% (w/v) |
| Polysorbate 20 | 3.00% (w/v) |
| Poloxamer 407 | 9.00% (w/v) |
| Water to 100 ml | |

The compositions of this invention are useful for the preparation of ready to use collyria.

The collyrium of this invention may comprise additional conventional pharmaceutical excipients suitable for ophthalmic use.

Examples of conventional excipients are the preservatives, buffers, chelating agents, antioxidants, salts for regulating the osmotic pressure, regulators of viscosity and the lubricants.

The preparation of the pharmaceutical compositions of this invention is carried out according to conventional techniques.

Preferably, the therapeutically effective concentration of each single active principle (i.e. AINS and decongestant) is of from 0.015% to 0.10% (w/v).

The following examples illustrate the present invention without limiting it in any way.

EXAMPLE 1

Preparation of a collyrium containing sodium diclofenac and tramazoline hydrochloride (Composition 1)

Polysorbate 20 (300 g) is poured in water (2L) and is stirred until a clear solution is obtained. Sodium diclofenac (10 g) is added to the solution under stirring and slow stirring is continued until a clear solution is obtained (solution A).

Tramazoline hydrochloride monohydrate (6.32 g) is poured in water (5 l) under stirring until a clear solution is obtained. Poloxamer 407 is added (900 g) under stirring and stirring is continued until a clear solution is obtained (solution B).

Always under stirring, solution A is added to solution B and the flask of solution A is further washed with water (1l). Stirring is continued until a clear solution is obtained (solution C).

Benzalkonium chloride (1 g), disodium EDTA (10 g), thimerosal (2 g), monopotassium phosphate (9 g), disodium phosphate dodecahydrate (70 g) and sodium chloride (15 g) are added under stirring to a flask containing slightly warm water (1L).

Stirring is continued until a clear solution is obtained (solution D).

Solution D is poured into solution C under slow stirring and the final volume is brought to 10L.

The solution is then filtered through a sterilizing filter and the sterile solution is subdivided into about 2000 vials.

Each vial contains a collyrium having the following composition:

| | |
|---|---|
| (A) Sodium diclofenac | 5.00 mg |
| (B) Tramazoline hydrochloride monohydrate | 3.16 mg |
| (C) Polysorbate 20 | 150.00 mg |
| (D) Poloxamer 407 | 450.00 mg |
| (E) Monopotassium phosphate | 4.50 mg |
| (F) Disodium phosphate dodecahydrate | 35.00 mg |
| (G) Disodium EDTA | 5.00 mg |
| (H) Benzalkonium chloride | 0.50 mg |
| (I) Thimerosal | 1.00 mg |
| (J) Sodium chloride | 7.50 mg |
| (K) Injectable water to 5 ml | |

EXAMPLE 2

Preparation of a collyrium containing indomethacin and tramazoline hydrochloride (Composition 2)

Following the procedure of Example 1 a collyrium is prepared having the same composition as in Example 1 except that component (A) is replaced by indomethacin (5.00 mg).

EXAMPLE 3

Preparation of a collyrium containing flurbiprofen and tramazoline hydrochloride (Composition 3)

Following the procedure of Example 1 a collyrium is prepared having the same composition as in Example 1 except that component (A) is replaced by flurbiprofen (1.50 mg).

EXAMPLE 4

Preparation of a collyrium containing sodium diclofenac and tetrahydrozoline hydrochloride (Composition 4)

Following the procedure of Example 1 a collyrium is prepared having the same composition as in Example 1 except that component (B) is replaced by tetrahydrozoline hydrochloride (2.50 mg).

EXAMPLE 5

Preparation of a collyrium containing indomethacin and tetrahydrozoline hydrochloride (Composition 5)

Following the procedure of Example 1 a collyrium is prepared having the same composition as in Example 2 except that component (B) is replaced by tetrahydrozoline hydrochloride (2.50 mg).

EXAMPLE 6

Preparation of a collyrium containing flurbiprofen and tetrahydrozoline hydrochloride (Composition 6)

Following the procedure of Example 1 a collyrium is prepared having the same composition as in Example 3 except that component (B) is replaced by tetrahydrozoline hydrochloride (2.50 mg).

EXAMPLE 7

Preparation of comparison collyria

Following the procedure of Example 1 the following collyria have been prepared:

Composition 1-R having the same composition as in Example 1 except that the amount of component (C) is of 50.00 mg and component (D) is absent.

Composition 2-R having the same composition as in Example 1 except that component (D) is absent.

Composition 3-R having the same composition as in Example 1 except that the amount of component (C) is of 450.00 mg and component (D) is absent.

Composition 4-R having the same composition as in Example 1 except that the amount of component (C) is of 600.00 mg and component (D) is absent.

Composition 5-R having the same composition as in Example 1 except that the amount of component (C) is of 750.00 mg and component (D) is absent.

Composition 6-R having the same composition as in Example 1 except that the amount of component (C) is of 100.00 mg and component (D) is replaced by polyethylene glycol 300 (500.00 mg).

Composition 7-R having the same composition as in Example 1 except that component (D) is replaced by polyethylene glycol 6000 (500.00 mg).

Composition 8-R having the same composition as in Example 1 except that component (D) is replaced by glycerol (100.00 mg).

Composition 9-R having the same composition as in Example 1 except that component (D) is replaced by propylene glycol (100.00 mg).

Composition 10-R having the same composition as in Example 1 except that component (D) is replaced by polyoxyethylene(50) monostearate (100.00 mg).

Composition 11-R having the same composition as in Example 1 except that component (D) is replaced by nonoxynol (150.00 mg).

Composition 12-R having the same composition as in Example 1 except that component (D) is replaced by sorbitan mono-oleate (150.00 mg).

EXAMPLE 8

Stability tests

The compositions of this invention and the comparison collyria have been stored at room temperature and the possible formation of a precipitate has been monitored.

Table 1 shows the results of the stability tests on the comparison collyria.

TABLE 1

| Composition | Appearance at the end of the preparation process | Formation of a precipitate |
| --- | --- | --- |
| 1-R | solution | instantaneous |
| 2-R | solution | 1 hour |
| 3-R | solution | 18 hours |
| 4-R | solution | 36 hours |
| 5-R | solution | 6 months |
| 6-R | suspension | — |
| 7-R | solution | 2–3 hours |
| 8-R | suspension | — |
| 9-R | suspension | — |
| 10-R | suspension | — |
| 11-R | solution | 3 hours |
| 12-R | suspension | — |

After 1 year under the same storage conditions, the compositions 1, 2, 3, 4, 5 and 6 of this invention did not form any precipitate.

The compositions of this invention were unchanged even after 1 year at higher temperatures (30°–400° C.).

These results anticipate that the compositions of this invention are stable at room temperature for more than 2 years.

We claim:

1. A pharmaceutical aqueous solution for ophthalmic use comprising (i) a nonsteroidal anti-inflammatory drug having a carboxylic group, selected from the group consisting of diclofenac, flurbiprofen, indomethacin, suprofen, ketorolac, and pharmaceutically acceptable isomers and salts thereof, (ii) tramazoline, and (iii) a mixture of polysorbate 20 and poloxamer 407.

2. A pharmaceutical composition according to claim 1, wherein the mixture of a polysorbate 20 and a poloxamer 407 is made of 1 part by weight of polysorbate 20 and 3 parts by weight of poloxamer 407.

* * * * *